United States Patent
Ali et al.

(10) Patent No.: US 12,083,153 B1
(45) Date of Patent: Sep. 10, 2024

(54) **SILVER NANOPARTICLE COMPOSITION INCLUDING BIOSYNTHESIZED SILVER NANOPARTICLES AND AN EXTRACT OF *FARSETIA AEGYPTIACA***

(71) Applicant: KING FAISAL UNIVERSITY, Al-Ahsa (SA)

(72) Inventors: Enas M. Ali, Hofouf (SA); Basem M. Abdallah, Hofouf (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/534,062

(22) Filed: Dec. 8, 2023

(51) Int. Cl.
| | |
|---|---|
| A61K 36/31 | (2006.01) |
| A61K 9/51 | (2006.01) |
| A61K 33/38 | (2006.01) |
| A61K 41/00 | (2020.01) |
| A61P 31/10 | (2006.01) |

(52) U.S. Cl.
CPC .............. *A61K 36/31* (2013.01); *A61K 9/51* (2013.01); *A61K 9/5192* (2013.01); *A61K 33/38* (2013.01); *A61K 41/00* (2013.01); *A61P 31/10* (2018.01)

(58) Field of Classification Search
CPC ..................................................... A61K 36/31
See application file for complete search history.

(56) References Cited

FOREIGN PATENT DOCUMENTS

| | | |
|---|---|---|
| DE | 102008064365 A1 | 6/2010 |
| DE | 202010006267 U1 | 12/2010 |

OTHER PUBLICATIONS

Dhaka et al, Balanites aegyptiaca leaf extract mediated synthesis of silver nanoparticles and their catalytic dye degradation and antifungal activity, (Year: 2022).*

Atta et al, A novel flavanoid compound from Farsetia aegyptiaca, (Year: 2013).*

Atta, E. M.; Hashem, A. I.; Eman, and R. El-Sharkawy, A novel flavonoid compound from Farsetia aegyptia and its antimicrobial activity. DOI:10.1007/s10600-013-0631-z ; 2023.

Anita Dhaka, Shani Raj, Chanda kumari Githala, Suresh Chand Mali and Rohini Trivedi. Balanites aegyptiaca leaf extract-mediated synthesis of silver nanoparticles and their catalytic dye degradation and antifungal efficacy. doi.org/10.3389/fbioe.2022.977101; 2023.

Mohd Sayeed Akhtar, Jitendra Panwar, and Yeoung-Sang Yun, Biogenic Synthesis of Metallic Nanoparticles by Plant Extracts, https://doi.org/10.1021/sc300118u; 2023.

Rajesh Kotcherlakota, Sourav Das, and Chitta Ranjan Patra, Green Synthesis, Characterization and Applications of Nanoparticles Therapeutic applications of green-synthesized silver nanoparticles. doi: 10.1016/B978-0-08-102579-6.00017-4 ; 2023.

(Continued)

*Primary Examiner* — Carlos A Azpuru
(74) *Attorney, Agent, or Firm* — Nath, Goldberg & Meyer; Joshua B. Goldberg

(57) ABSTRACT

A silver nanoparticle composition for controlling or inhibiting the growth of *P. jirovecii* can include biosynthesized silver nanoparticles and an extract of *Farsetia aegyptiaca* (FA). The biosynthesized silver nanoparticles can be *Farsetia aegyptiaca* silver nanoparticles (Fa-AgNPs) prepared using an extract of *Farsetia aegyptiaca* (FA). In an embodiment, the *Farsetia aegyptiaca* silver nanoparticles (Fa-AgNPs) can have particle sizes ranging from about 10 nm to about 35 nm.

10 Claims, 2 Drawing Sheets

FA-AgNPs/FA

(56) References Cited

OTHER PUBLICATIONS

Magdalena Wypij, Tomasz Jędrzejewski, Joanna Trzcińska-Wencel, Maciej Ostrowski, Mahendra Rai1, and Patrycja Golińska, Green Synthesized Silver Nanoparticles: Antibacterial and Anticancer Activities, Biocompatibility, and Analyses of Surface-Attached Proteins. DOI: 10.3389/fmicb.2021.632505.

Ana Luísa Tomás, Miguel P. de Almeida, Fernando Cardoso, Mafalda Pinto, Eulália Pereira, Ricardo Franco, Olga Matos, Development of a Gold Nanoparticle-Based Lateral-Flow Immunoassay for Pneumocystis Pneumonia Serological Diagnosis at Point-of-Care. DOI: 10.3389/fmicb.2019.02917.

* cited by examiner

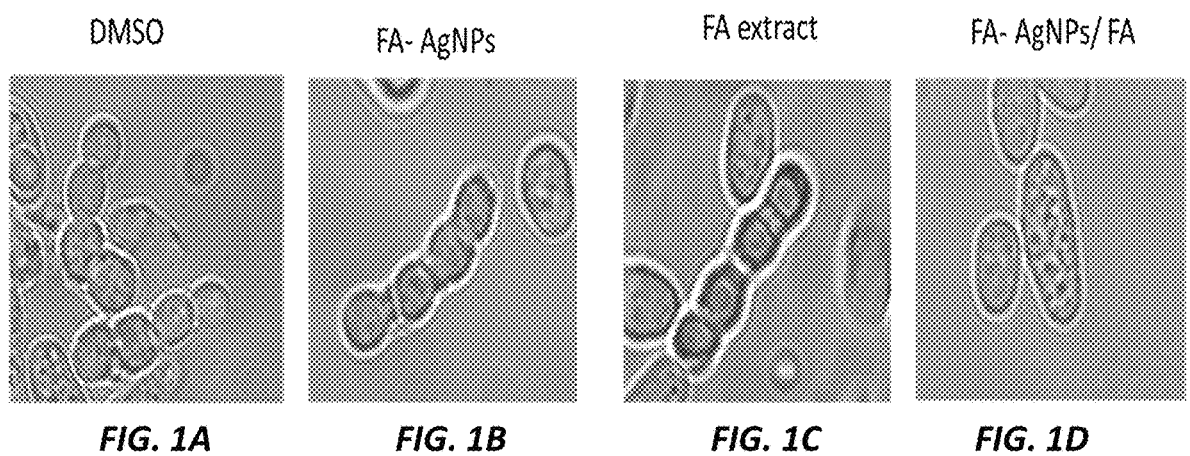
| DMSO | FA-AgNPs | FA extract | FA-AgNPs/FA |
|---|---|---|---|
| FIG. 1A | FIG. 1B | FIG. 1C | FIG. 1D |
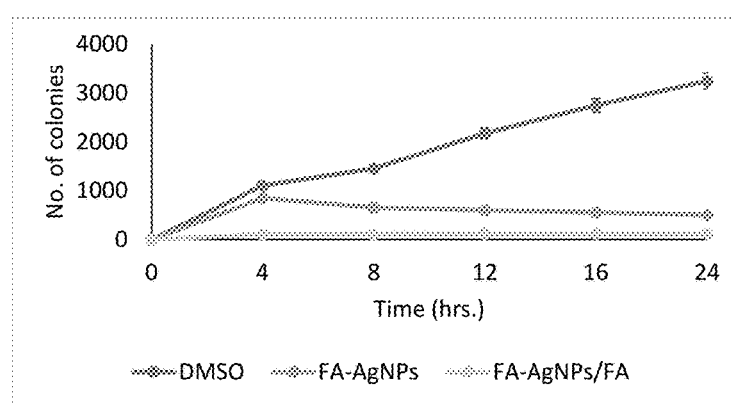
FIG. 2

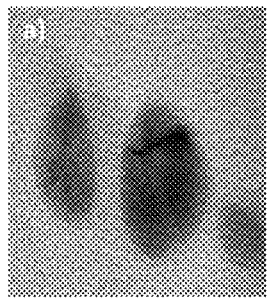 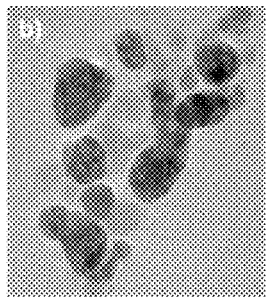 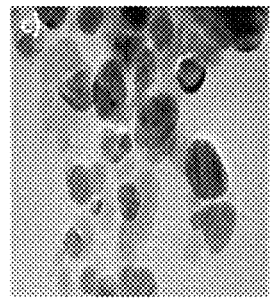 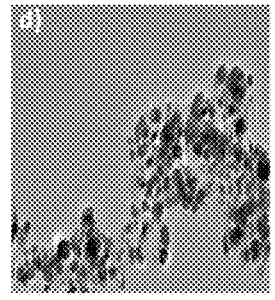
*FIG. 3A*  *FIG. 3B*  *FIG. 3C*  *FIG. 3D*
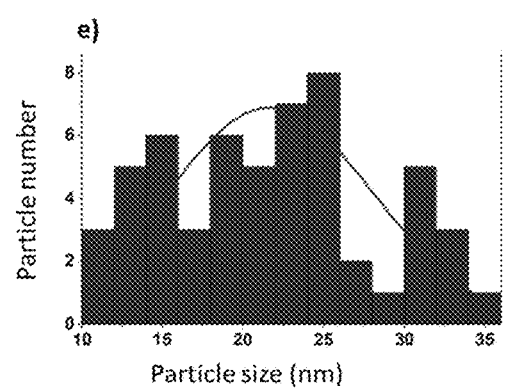
*FIG. 3E*

SILVER NANOPARTICLE COMPOSITION INCLUDING BIOSYNTHESIZED SILVER NANOPARTICLES AND AN EXTRACT OF FARSETIA AEGYPTIACA

BACKGROUND

1. Field

The disclosure of the present patent application relates to silver nanoparticles, and particularly, to a silver nanoparticles composition including biosynthesized silver nanoparticles and an extract of Farsetia aegyptiaca.

2. Description of the Related Art

Recently, nanoparticles have demonstrated important uses in a variety of fields. Nanoparticles have been used in electronics, sensing, optics, and medicine, for example.

Synthesis of nanoparticles has been achieved by a variety of methods, including physicochemical, thermal decomposition, electrochemical, microwave assisted, sonochemical, solvothermal, photosynthesis, photochemical reduction, chemical reduction, and continuous-flow methods. These methods are often costly or produce by-products that pose increased risks to human health and the environment.

In recent years, green or environmentally friendly chemical methods have been developed to prepare nanoparticles using plant extracts. Green chemistry has the advantage of being safer, faster, environmentally friendly, and economical. However, the rise of green methods of preparing nanoparticles has also demonstrated that the activities and characteristics of the nanoparticles vary significantly, depending upon the detailed method of synthesis and specific plant extract used.

Pneumocystis jirovecii is a fungus that causes pneumocystis pneumonia in humans, which remains a leading opportunistic infection associated with AIDS subjects. Additionally, pneumocystis pneumonia increasingly targets subjects with underlying chronic disease states, such as chronic obstructive pulmonary disorder, subjects receiving anti-TNF therapy, and other immunosuppressive agents. However, despite concerted efforts towards identification of new chemotherapeutic agents, trimethoprim-sulfamethoxazole remains the standard prophylactic and therapeutic modality in use today. With such a limited repertoire of therapeutic options, there is a great potential for developing resistance to this compound by the pathogen.

Thus, nanoparticles synthesized using an environmentally friendly method solving the aforementioned problems are desired.

SUMMARY

The present subject matter relates to a silver nanoparticle composition for controlling or inhibiting the growth of P. jirovecii. The silver nanoparticle composition can include biosynthesized silver nanoparticles and an extract of Farsetia aegyptiaca (FA). The biosynthesized silver nanoparticles can be Farsetia aegyptiaca silver nanoparticles (Fa-AgNPs) prepared using an extract of Farsetia aegyptiaca (FA). In an embodiment, the extract of Farsetia aegyptiaca (FA) can be a leaf extract of Farsetia aegyptiaca (FA). In one embodiment, the leaf extract of Farsetia aegyptiaca (FA) can be an alcohol extract, e.g., an ethanolic extract.

According to an embodiment, the silver nanoparticle composition, or Farsetia aegyptiaca silver nanoparticle composition (FA-AgNPs/FA), can be prepared by providing a Farsetia aegyptiaca extract, mixing the Farsetia aegyptiaca extract with silver nitrate, heating the mixture to provide the Farsetia aegyptiaca silver nanoparticles, and mixing the Farsetia aegyptiaca silver nanoparticles with an Farsetia aegyptiaca extract to provide the Farsetia aegyptiaca silver nanoparticle composition. In an embodiment, the Farsetia aegyptiaca silver nanoparticles can be used to treat or inhibit a fungal infection. In an embodiment, the fungal infection can be pneumocystis pneumonia caused by Pneumocystis jirovecii.

In an embodiment, the present subject matter relates to a method of synthesizing Farsetia aegyptiaca silver nanoparticles, comprising: mixing a Farsetia aegyptiaca extract with a silver nitrate solution to provide a mixture, heating the mixture to obtain a heated solution including Farsetia aegyptiaca silver nanoparticles, and isolating the Farsetia aegyptiaca silver nanoparticles from the heated solution.

According to an embodiment, the present subject matter relates to silver nanoparticles prepared by the methods as described herein.

According to an embodiment, the present subject matter relates to a pharmaceutical composition comprising the Farsetia aegyptiaca silver nanoparticle composition and a pharmaceutically acceptable carrier. In an embodiment, a method of treating pneumocystis pneumonia comprises administering a therapeutically effective amount of the pharmaceutical composition as described herein to a subject in need thereof.

These and other features of the present subject matter will become readily apparent upon further review of the following specification and drawings.

BRIEF DESCRIPTION OF THE DRAWINGS

FIGS. 1A-1D are images of the effect of (1A) control (DMSO); (1B) Farsetia aegyptiaca silver nanoparticles (FA FA-AgNPs); (1C) plant extract (FA), and (1D) composition including Farsetia aegyptiaca silver nanoparticles and Farsetia aegyptiaca extract (FA-AgNPs/FA) on sporulation of P. jirovecii.

FIG. 2 is a graph of a time kill assay showing the effect of the plant extract (FA), FA-AgNPs, and FA-AgNPs/FA on growth of P. jirovecii.

FIGS. 3A-3E are transmission electron microscopy (TEM) micrographs showing the size of biosynthesized FA-AgNPs using scale bars (FIG. 3A) 10 nm; (FIG. 3B) 20 nm; (FIG. 3C) 50 nm; and (3D) 100 nm; and FIG. 3E is a histogram of the TEM images (100 nm).

DETAILED DESCRIPTION OF THE PREFERRED EMBODIMENTS

The following definitions are provided for the purpose of understanding the present subject matter and for construing the appended patent claims.

Definitions

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

A "subject" herein is typically a human. In certain embodiments, a subject is a non-human mammal. Exemplary non-human mammals include laboratory, domestic, pet, sport, and stock animals, e.g., mice, cats, dogs, horses, and cows. As used herein, the term "subject" refers to any single subject for which treatment is desired. In certain embodiments, the subject herein is a human. A subject can be considered to be in need of treatment.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

The present subject matter relates to a silver nanoparticle composition for controlling or inhibiting the growth of *P. jirovecii*. The silver nanoparticle composition can include biosynthesized silver nanoparticles and an extract of *Farsetia aegyptiaca* (FA). The biosynthesized silver nanoparticles can be *Farsetia aegyptiaca* silver nanoparticles (Fa-AgNPs) prepared using an extract of *Farsetia aegyptiaca* (FA). In an embodiment, the *Farsetia aegyptiaca* silver nanoparticles (Fa-AgNPs) can be polydispersed and have a shape that is spherical or oval. In an embodiment, the *Farsetia aegyptiaca* silver nanoparticles (Fa-AgNPs) can have particle sizes ranging from about 10 nm to about 35 nm.

In an embodiment, the extract of *Farsetia aegyptiaca* (FA) can be a leaf extract of *Farsetia aegyptiaca* (FA). In one embodiment, the leaf extract of *Farsetia aegyptiaca* (FA) can be an alcohol extract, e.g., an ethanolic extract.

In an embodiment, the extract may be synthesized by harvesting *Farsetia aegyptiaca* leaves, drying the *Farsetia aegyptiaca* leaves, powdering the dried *Farsetia aegyptiaca* leaves, mixing the powdered *Farsetia aegyptiaca* leaves with a solvent to provide a solution, and extracting the solution to provide a plant extract. In an embodiment, the solvent can be an alcohol, e.g., ethanol. In an embodiment, extracting the solution can include concentrating the solution using a rotary evaporator to obtain the extract of *Farsetia. aegyptiaca*.

The silver nitrate, e.g., an aqueous solution of silver nitrate, can be added to the plant extract to provide a mixture including the *Farsetia. aegyptiaca* silver nanoparticles. The mixture can be heated to provide a heated solution including *Farsetia aegyptiaca* silver nanoparticles. In an embodiment, the mixture can be heated using a microwave oven operating at a power ranging from about 9000 W to about 1300 W and a frequency ranging from about 2000 MHz to about 3000 MHz for a period of time ranging from about 100 seconds to about 200 seconds. In an embodiment, the mixture can be heated using a microwave oven operating at a power of 1000 W and a frequency 2500 MHz. In an embodiment, the mixture can be subjected to microwave irradiation for about 120 seconds.

According to an embodiment, isolating the *Farsetia aegyptiaca* silver nanoparticles from the heated solution can include centrifuging the solution at about 1000 rpm to about 2000 rpm for about 10 minutes to about 20 minutes. In one embodiment, the heated solution can be centrifuged for about 13 minutes at about 1500 rpm. The supernatant can be decanted and the nanoparticles can be redispersed in water. The process can be repeated to further purify the product. The purified product can be dried, e.g., by freeze-drying.

In an embodiment, about 100 mL solution of silver nitrate ($AgNO_3$) (about 10 mM) can be added to about a 200 mL solution of the plant extract (about 500 µg/mL) to provide the mixture. In an embodiment the solution of silver nitrate is an aqueous solution. The silver nitrate can reduce the plant extract into $Ag+$ ions. In an embodiment, the mixture can be heated to provide a *Farsetia aegyptiaca* nanoparticle composition (FA-AgNPs).

An embodiment of the present subject matter is directed to a pharmaceutical composition comprising the *Farsetia aegyptiaca* silver nanoparticle composition and a pharmaceutically acceptable carrier.

An embodiment of the present subject matter is directed to a method of making a pharmaceutical composition including mixing the *Farsetia aegyptiaca* silver nanoparticle composition with a pharmaceutically acceptable carrier. For example, the method of making a pharmaceutical composition can include mixing the *Farsetia aegyptiaca* silver nanoparticle composition under sterile conditions with a pharmaceutically acceptable carrier with preservatives, buffers, and/or propellants to create the pharmaceutical composition.

To prepare the pharmaceutical composition, the *Farsetia aegyptiaca* silver nanoparticle composition, as the active ingredient, is intimately admixed with a pharmaceutically acceptable carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents, and the like. Further, for solid oral preparations, suitable carriers and additives include starches, sugars, diluents, granulating agents, lubricants, binders, disintegrating agents, and the like.

The present compositions can be in unit dosage forms such as tablets, pills, capsules, powders, granules, ointments, sterile parenteral solutions or suspensions, metered aerosol or liquid sprays, drops, ampules, auto-injector devices or suppositories, for oral parenteral, intranasal, sublingual or rectal administration, or for administration by inhalation or insufflation. The *Farsetia aegyptiaca* silver nanoparticle composition be mixed under sterile conditions with a pharmaceutically acceptable carrier and, if required, any needed preservatives, buffers, or propellants. The composition can be presented in a form suitable for daily, weekly, or monthly administration. The pharmaceutical compositions herein will contain, per dosage unit, e.g., tablet, capsule, powder, injection, teaspoonful, suppository and the like, an amount of the active ingredient necessary to deliver an effective dose. A therapeutically effective amount of the *Farsetia aegyptiaca* silver nanoparticle composition or an amount effective to treat a disease, such as a fungal infection, may be determined initially from the Examples described herein and adjusted for specific targeted diseases using routine methods.

The *Farsetia aegyptiaca* silver nanoparticle composition can have antifungal properties. In an embodiment, the *Farsetia aegyptiaca* silver nanoparticle composition can be administered to a subject in need thereof to inhibit fungal growth. In an embodiment, the *Farsetia aegyptiaca* silver nanoparticle composition can inhibit the growth of *P. jirovecii*. In an embodiment, the *Farsetia aegyptiaca* silver nanoparticle composition can be administered to a subject in need thereof to treat a fungal infection, such as *pneumocystis* pneumonia. In a further embodiment, the *Farsetia aegyptiaca* silver nanoparticle composition can be administered to a subject in need thereof to treat *pneumocystis* pneumonia. In an embodiment, the *Farsetia aegyptiaca* silver nanoparticle composition can be formulated as an aerosol for administration to a subject in need thereof.

An embodiment of the present subject matter is directed to a method of inhibiting fungal growth in a subject, comprising administering to a subject in need thereof a therapeutically effective amount of the pharmaceutical composition according to the present subject matter. In an embodiment, the present subject matter is directed to a method of treating a fungal infection in a subject, comprising administering to a subject in need thereof a therapeutically effective amount of the pharmaceutical composition according to the present subject matter. In an embodiment, the fungal infection is *pneumocystis* pneumonia.

The *Farsetia aegyptiaca* silver nanoparticle composition or pharmaceutical compositions thereof can be administered to a subject by any suitable route. For example, the compositions can be administered orally (including bucally and sublingually), nasally, rectally, intracisternally, intra vaginally, intraperitoneally, topically, transdermally (as by powders, ointments, or drops), and/or parenterally. As used herein, "parenteral" administration refers to modes of administration other than through the gastrointestinal tract, which include intravenous, intramuscular, intraperitoneal, intrasternal, intramammary, intraocular, retrobulbar, intrapulmonary, intrathecal, subcutaneous and intraarticular injection and infusion. Surgical implantation may also be contemplated, including, for example, embedding a composition of the disclosure in the body such as, for example, in a tissue, in the abdominal cavity, under the splenic capsule, brain, or in the cornea.

The present teachings are illustrated by the following examples.

Example 1

Silver Nanoparticle Composition Synthesis Using *Farsetia aegyptiaca*

An ethanolic extract of *Farsetia aegyptiaca* was prepared by drying *Farsetia aegyptiaca* leaves using a drying hood and reducing the dried leaves to a powder using a blender. The leaf powder was percolated with ethanol (95%) to obtain a product. The product was concentrated using a rotary evaporator to obtain the ethanolic extract.

A 20 mL solution of the ethanolic leaf extract of *Farsetia aegyptiaca* was mixed with a 100 mL solution of silver nitrate ($AgNO_3$) (1 mM). The two solutions were mixed and microwaved at 1000 W and a frequency of 2500 MHz for 120 seconds. The formation of AgNPs was monitored using UV-vis spectrophotometer by analyzing the reaction mixture after 40 seconds, 80 seconds, and 120 seconds of microwave action. The *Farsetia aegyptiaca* silver nanoparticles FA-AgNPs were separated by centrifugation at 15,000 g for 13 minutes. The supernatant was decanted, and the nanoparticles were redispersed in distilled water. The process was repeated two times. The purified sample thus obtained was freeze-dried to provide a dry sample. AgNPs formed using *Farsetia aegyptiaca* were characterized by transmission electron microscopy (TEM). The TEM images (FIGS. 3A-3D) displayed that the biosynthesized FA-AgNPs are polydisperse and are mostly spherical and oval in shape with particle sizes ranging from 10 nm to 35 nm (FIG. 3E).

Example 2

Activity Against *P. jirovecii*

The effect of the biosynthesized silver nanoparticles alone, plant extract alone, and the composition including the biosynthesized silver nanoparticles and the plant extract on sporulation of *P. jirovecii* were examined. The results (FIG. 1) demonstrated that sporulation is completely inhibited when *P. jirovecii* was exposed to the composition including the biosynthesized silver nanoparticles and the plant extract (FA-AgNPs/FA) as compared to the plant extract alone or the biosynthesized silver nanoparticles (FA-AgNPs) alone. Additionally, time-kill curves showed the fungistatic action of the composition including both the FA-AgNPs and the leaf extract (FA) at 100 and 200 µg/mL, respectively, on the growth of *P. jirovecii* cells (FIG. 2). After 8 hours of incubation, the composition (FA-AgNPs/FA) completely repressed the growth of *P. jirovecii*. Therefore, the composition (FA-AgNPs/FA) exhibited a synergetic antifungal action that exceeded levels achieved by each of the FA-AgNPs and the plant extract alone.

It is to be understood that the silver nanoparticle composition is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A silver nanoparticle composition, comprising: *Farsetia aegyptiaca* silver nanoparticles (Fa-AgNPs) and an extract of *Farsetia aegyptiaca* (FA).

2. The silver nanoparticle composition of claim 1, wherein the extract of *Farsetia aegyptiaca* silver is an alcohol extract of the leaf of *Farsetia aegyptiaca*.

3. The silver nanoparticle composition of claim 1, wherein the *Farsetia aegyptiaca* silver nanoparticles are formed by providing an extract of *Farsetia aegyptiaca* and mixing the extract of *Farsetia aegyptiaca* with silver nitrate to provide the *Farsetia aegyptiaca* silver nanoparticles.

4. The silver nanoparticle composition of claim 1, wherein the silver nanoparticles have a particle size ranging from about 10 nm to about 35 nm.

5. A method of synthesizing a silver nanoparticle composition, comprising:
    mixing a *Farsetia aegyptiaca* extract with a silver nitrate solution to provide a mixture;
    heating the mixture to obtain a heated solution including *Farsetia aegyptiaca* silver nanoparticles; and
    mixing the *Farsetia aegyptiaca* silver nanoparticles with a *Farsetia aegyptiaca* extract to provide the silver nanoparticle composition.

6. The method of claim 5, wherein heating the *Farsetia aegyptiaca* mixture comprises subjecting the *Farsetia aegyptiaca* mixture to microwave irradiation.

7. The method of claim 5, further comprising isolating the *Farsetia aegyptiaca* silver nanoparticles from the heated solution by centrifuging the heated solution including the *Farsetia aegyptiaca* silver nanoparticles to separate the *Farsetia aegyptiaca* silver nanoparticles from the heated solution.

8. The method of claim 7, wherein the heated solution is centrifuged at about 1000 rpm to about 2000 rpm for about 10 minutes to about 20 minutes.

9. The method of claim 5, wherein the *Farsetia aegyptiaca* extract is a *Farsetia aegyptiaca* leaf extract.

10. A silver nanoparticle composition prepared according to the method of claim 5.

* * * * *